United States Patent
Sablone (10) Patent No.: US 9,408,754 B2
(45) Date of Patent: Aug. 9, 2016

(54) PROCESS FOR PRODUCING SANITARY ARTICLES THAT CAN BE WORN AS A PAIR OF PANTS, AND CORRESPONDING INTERMEDIATE PRODUCT

(75) Inventor: Gabriele Sablone, Pescara (IT)

(73) Assignee: FAMECCANICA.DATA S.P.A., Pescara (IT)

( * ) Notice: Subject to any disclaimer, the term of this patent is extended or adjusted under 35 U.S.C. 154(b) by 349 days.

(21) Appl. No.: 13/578,884

(22) PCT Filed: Feb. 8, 2011

(86) PCT No.: PCT/IB2011/050522
§ 371 (c)(1),
(2), (4) Date: Aug. 14, 2012

(87) PCT Pub. No.: WO2011/101772
PCT Pub. Date: Aug. 25, 2011

(65) Prior Publication Data
US 2012/0310198 A1 Dec. 6, 2012

(30) Foreign Application Priority Data
Feb. 16, 2010 (IT) .............................. TO2010A0111

(51) Int. Cl.
*B32B 37/00* (2006.01)
*A61F 13/15* (2006.01)
(Continued)

(52) U.S. Cl.
CPC ..... *A61F 13/15756* (2013.01); *A61F 13/15699* (2013.01); *A61F 13/15739* (2013.01);
(Continued)

(58) Field of Classification Search
CPC ............... A61F 13/15577; A61F 13/15585; A61F 13/15756; A61F 13/15699; A61F 13/15723; A61F 13/15739; A61F 13/49012; A61F 13/49014; A61F 13/49015; A61F 2013/15715; A61F 2013/49044; A61F 2013/49047; A61F 2013/49049; A61F 2013/4905

USPC ........................................................... 604/389
See application file for complete search history.

(56) References Cited

U.S. PATENT DOCUMENTS 5,580,411 A 12/1996 Nease et al.
5,705,013 A 1/1998 Nease et al.
(Continued)

FOREIGN PATENT DOCUMENTS

EP 1 719 484 11/2006
EP 1 941 853 7/2008
(Continued)

OTHER PUBLICATIONS

International Search Report for PCT/IB2011/050522 mailed May 26, 2011.
(Continued)

*Primary Examiner* — Lynne Anderson
(74) *Attorney, Agent, or Firm* — Nixon & Vanderhye P.C.

(57) ABSTRACT

The process enables production of sanitary articles that can be worn as a pair of pants (such as, for instance, nappies or bariatric pants) comprising a central body (2), which can be set in a concave configuration around the crotch region of the user and at least one pair of side panels (3, 4), which are connected to the central body (2) and are to define at least in part the waistband of the article (1). The process envisages obtaining an intermediate product constituted by one or more assembly webs (1000; 1000*a*, 1000*b*) which carries/carry applied thereon, on at least one of its sides, a plurality of said side panels (3, 4), each having a proximal edge (6) applied on said assembly web (1000; 1000*a*, 1000*b*). The side panels (3, 4) are connected to the central body (2) by connecting to the central body (2) itself a portion of assembly web (1000; 1000*a*; 1000*b*) which carries applied thereon a respective side panel (3, 4).

24 Claims, 9 Drawing Sheets

(51) Int. Cl.
  *A61F 13/56* (2006.01)
  *A61F 13/49* (2006.01)

(52) U.S. Cl.
  CPC ......... *A61F13/565* (2013.01); *A61F 13/49015* (2013.01); *A61F 2013/15715* (2013.01); *Y10T 156/10* (2015.01); *Y10T 156/1051* (2015.01); *Y10T 156/1052* (2015.01)

(56) References Cited

U.S. PATENT DOCUMENTS

| | | | |
|---|---|---|---|
| 7,517,572 B2* | 4/2009 | Van Dyke | 428/43 |
| 7,658,813 B2* | 2/2010 | Petersen | 156/253 |
| 7,871,400 B2* | 1/2011 | Sablone et al. | 604/385.01 |
| 7,901,534 B2* | 3/2011 | Gaston et al. | 156/256 |
| 7,918,961 B2* | 4/2011 | Wada et al. | 156/259 |
| 8,454,782 B2* | 6/2013 | Ostertag | 156/204 |
| 8,556,878 B2* | 10/2013 | Malowaniec et al. | 604/387 |
| 2005/0256497 A1* | 11/2005 | Gottwald et al. | 604/386 |
| 2006/0027306 A1 | 2/2006 | Olsson et al. | |
| 2006/0271004 A1* | 11/2006 | Petersen | 604/372 |
| 2007/0142808 A1 | 6/2007 | Wada et al. | |
| 2008/0060174 A1* | 3/2008 | Erdman et al. | 24/442 |
| 2008/0161766 A1 | 7/2008 | Sablone et al. | |
| 2012/0028777 A1* | 2/2012 | Knecht | 493/393 |

FOREIGN PATENT DOCUMENTS

| | | |
|---|---|---|
| JP | 2006-055382 | 3/2006 |
| JP | 2006-511303 | 4/2006 |
| JP | 2009-519089 | 5/2009 |
| WO | WO 96/24319 | 8/1996 |
| WO | WO 97/32552 | 9/1997 |
| WO | WO2007-072386 | 6/2007 |
| WO | WO 2008/081237 A1 | 7/2008 |

OTHER PUBLICATIONS

Written Opinion of the International Searching Authority mailed May 26, 2011.
English Translation of Chinese Second Office Action dated Jun. 23, 2014 issued in Chinese Patent Application No. 201180009527.5, 9 pp.
Translation of Japanese Office Action in Patent No. 2012552507 of Oct. 28, 2014.
Submission of prior art re 2012-552507 (in Japanese).
Notice of submission of prior art re 2012-552507 (in Japanese).
Japanese Office Action dated Jul. 28, 2015 for Japanese Patent Application No. 2012-552507 (with translation of Office Action and translation of claims).

* cited by examiner

PROCESS FOR PRODUCING SANITARY ARTICLES THAT CAN BE WORN AS A PAIR OF PANTS, AND CORRESPONDING INTERMEDIATE PRODUCT

This application is the U.S. national phase of International Application No. PCT/IB2011/050522 filed 8 Feb. 2011 which designated the U.S. and claims priority to IT TO2010A000111 filed 16 Feb. 2010, the entire contents of each of which are hereby incorporated by reference.

TEXT OF THE DESCRIPTION

1. Field of the Invention

The present description relates to the production of sanitary articles that can be worn as a pair of pants.

In particular, the description regards the production of sanitary articles comprising a central body, connected to which, at one end at least, is a pair of side panels.

2. Description of the Prior Art

Documents such as, for example, EP-A-1 941 853 describe processes for manufacturing sanitary articles that can be worn as a pair of pants and comprise:

- a central body (crotch portion), which can be set around the crotch region of the user, said central body extending in a longitudinal direction between two opposite ends; and
- at least one pair (and possibly two pairs) of side panels connected to one (and possibly to each) of the ends of said central body and extending on opposite sides of said central body to define at least in part the waistband of the article.

Said sanitary articles can be produced so that they are absorbent and comprise, set in the central body, an absorbent element (core). The side panels can also comprise an elasticated material, which is quite costly (or in any case of high quality) and of which it is in the interest of the manufacturer to minimize the waste.

The solution described in the document No. EP-A-1 941 853 envisages obtaining side panels that have a generally tapered configuration starting from the "proximal" edge (i.e., the edge that is to be connected to the central body) by segmenting a respective web element with cutting operations at least in part performed in a direction oblique with respect to the general direction of extension of said respective web element, and imparting, in alternating sequence on every other side panel thus formed, before applying it on the central body, a movement of rotation/overturning through 180°. After said movement of rotation/overturning, the panels are all oriented in the same way prior to their application on the central body of the article.

The solution described in the document No. EP-A-1 941 853 proves altogether satisfactory for the production of sanitary articles that are designed for newborn babies and small children, and also for a fair share of sanitary articles that are designed for use by incontinent adults.

Recently, however, the requirement of production of so-called "bariatric" sanitary articles, i.e., ones designed for obese adults, has been assuming increasing importance.

In these cases, the articles are of considerable size, for instance, approximately one meter long and approximately 90 cm wide, so as to reach circumferences of the waistband of the finished article even in the region of 180 cm.

The inventor has been able to note that the operations of manipulation, in particular of folding, of the side panels can prove very critical to be implemented in the presence of articles of these dimensions, also considering the very high production rates (hundreds of articles per minute) that it is in any case desired to maintain. However, irrespective of the dimensions of the article, there is perceived the need to produce articles that are cheaper than traditional articles (for example, by minimizing production waste) and present excellent characteristics of wearability.

OBJECT AND SUMMARY OF THE INVENTION

The object of the present invention is hence to provide a solution that will be able to overcome the critical aspects outlined above.

According to the invention, said object is achieved thanks to a process having the characteristics recalled in the ensuing claims.

The invention also regards a product that can be used for implementing the aforesaid process.

The claims form an integral part of the technical teaching provided herein in relation to the invention.

Various embodiments enable production of articles that are cheaper than traditional articles and present excellent characteristics of wearability. This not only regards articles for incontinent adults to which explicit reference has been made previously, but also in relation to articles for newborn babies and small children.

BRIEF DESCRIPTION OF THE ANNEXED DRAWINGS

The invention will now be described, purely by way of non-limiting example, with reference to the annexed drawings, wherein.

DETAILED DESCRIPTION OF EMBODIMENTS

Illustrated in the ensuing description are various specific details aimed at an in-depth understanding of the embodiments. The embodiments can be produced without one or more of the specific details, or with other methods, components, materials, etc. In other cases, known structures, materials or operations are not illustrated or described in detail herein so as not to render various aspects of the embodiments obscure.

The reference to "an embodiment" or "one embodiment" in the framework of the present description is intended to indicate that a particular configuration, structure, or characteristic described in relation to the embodiment is comprised in at least one embodiment. Furthermore, phrases such as "in an embodiment" or "in one embodiment" that may be present in different points of the present description do not necessarily refer to one and the same embodiment. Furthermore, particular conformations, structures, or characteristics can be adequately combined in one or more embodiments.

The references used herein are provided merely for convenience and hence do not define the sphere of protection or the scope of the embodiments.

In particular, as used herein, expressions such as "connect, connected" refer to the joining, connection, attachment, sealing, etc. of two elements. Two elements are herein considered connected together when they are joined together directly or indirectly in a permanent way, as in the case where each element is directly connected to intermediate elements.

Figure 1:
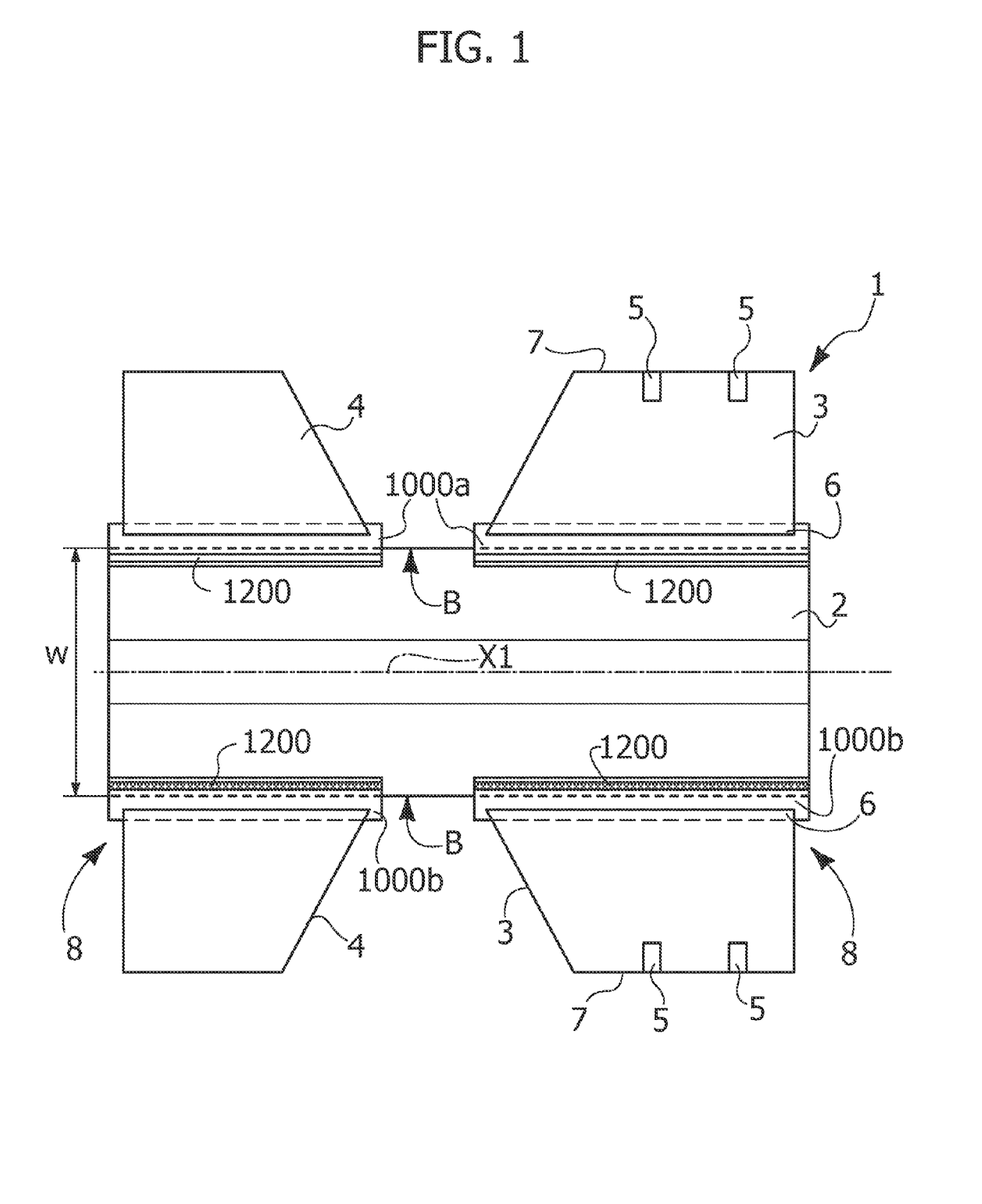
FIG. 1 illustrates an example of sanitary article according to one embodiment, represented in an unfolded position and stretched out.

FIG. 1 of the annexed drawings is a schematic representation of a sanitary article 1 that can be worn as a pair of pants. By way of reference, and without any limiting intention, the article 1 can be an absorbent article for incontinent adults.

The article 1, represented in FIG. 1 in a condition where it is unfolded and stretched out in a plane, comprises, according to a general configuration in itself known:

- a central body 2 (which, as will emerge more clearly in what follows, can be constituted by a topsheet permeable to liquids and by an impermeable backsheet, which are joined together with interposition of an absorbent structure), which can be set according to a general concave conformation around the crotch region of the user: the central body 2 extends in a longitudinal direction (main longitudinal axis X1 of the article 1) between two opposite ends and has a given width W in a transverse direction with respect to the aforesaid longitudinal direction X1;
- two (first) side panels 3 extending laterally on opposite sides from one of the ends of the central body 2; and
- two (second) side panels 4 extending laterally on opposite sides from the other end of the central body 2.

Figure 15:
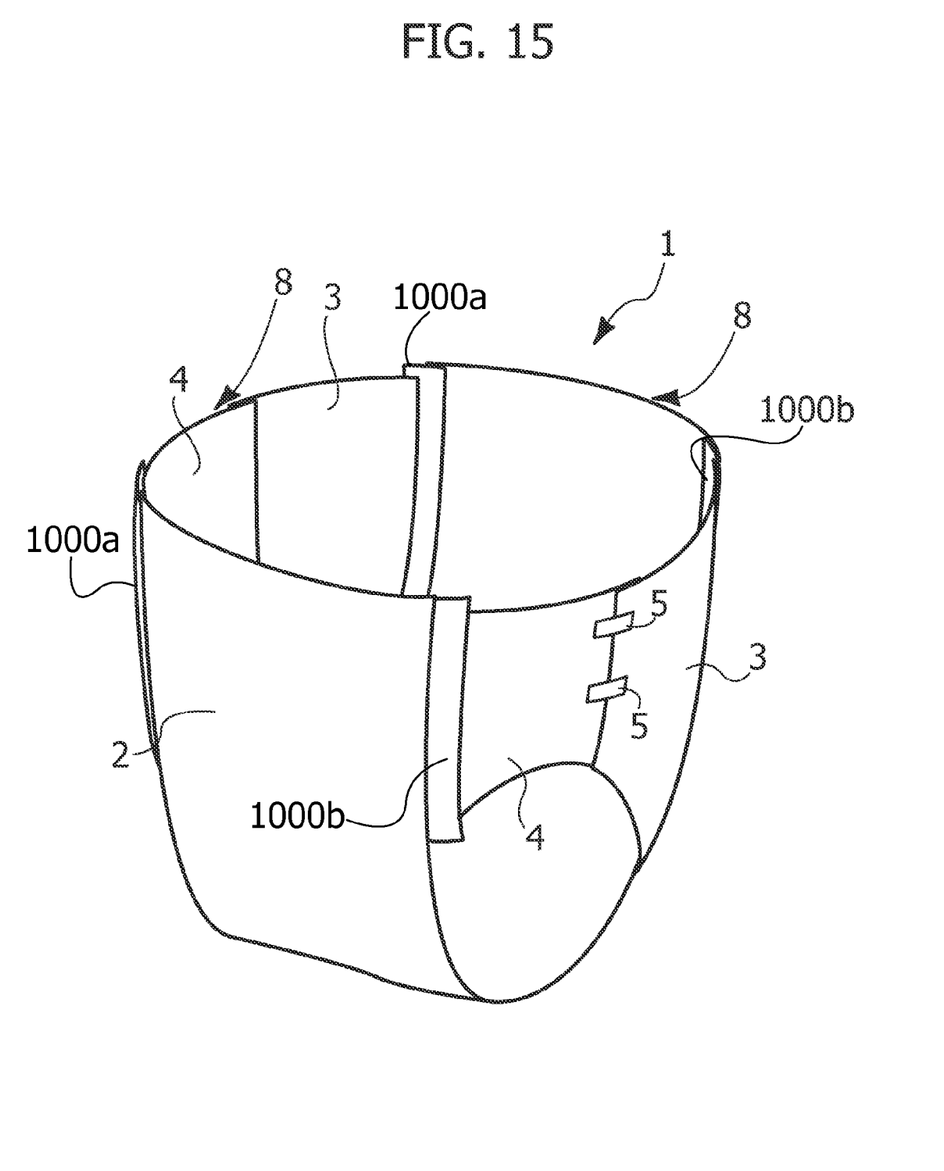
FIG. 15 illustrates an example of sanitary article according to one embodiment, represented in a closed position.

The side panels 3, 4 are connected to the central body 2 and are to define the waistband 8 of the article when the latter is worn as a pair of pants, as schematically represented in FIG. 15.

The specific characteristics of said elements are not in themselves important for the purposes of description and understanding of the embodiments.

By way of summary, it may be recalled that in various embodiments the main body 2 can comprise:

- a so-called topsheet permeable to body fluids, which is to come into contact with the body of the user;
- a so-called backsheet, which is to be positioned towards the outside of the article, i.e., in contact with the garments of the user; and
- an element of absorbent material (core) set between the topsheet and the backsheet, which can be connected to one another with adhesive.

The article 1 can be worn with the main body or central body 2 wrapped to form a U around the crotch region of the user, with the end from which the side panels 4 extend situated on the front of the user and the end from which the side panels 3 extend set in a position corresponding to the small of the back of the user.

The side panels 3 can then extend on the sides of the user so as to be connectable via closing systems comprising, for instance, adhesive formations 5 or hook-and-loop formations (commonly referred to as "Velcro") to the side panels 4 (see in this regard FIG. 15).

In various embodiments, the side panels 4 may be absent, and in this case the side panels 3 are to be connected directly to the front end of the central body 2.

Again, the relative position of the side panels 3 and of the side panels 4 can be reversed and, in this perspective, the terms "front" and "rear" are used herein only to distinguish the two pairs of side panels 3, 4 (if both are present) without this necessarily being understood as in any way limiting the modalities with which the article 1 is worn.

As has already been said, the side panels 4 may even be absent, and, even though this solution is seldom adopted, the side panels 3 could be localized at the end of the central body that is to be set on the front of the user.

Furthermore, in the case of sanitary articles of the pre-fastened type it is envisaged that the article is packaged and made available to the user in a closed condition, i.e., with the side panels 3 (and, if present 4) already closed along the waistband 8 of the article 1, as represented schematically in FIG. 15.

In the same way, as is well known to persons skilled in the sector, in addition to the aforesaid elements explicitly indicated herein, the article 1 can comprise numerous accessory elements, such as elastication elements, layers for acquisition of body fluids (the so-called "acquisition layers"), lateral formations for containing faeces (the so-called "cuffs") etc. This applies also as regards the details of embodiment of the topsheet, of the backsheet, and of the absorbent core, which can be produced according to a practically infinite range of possible embodiments amply documented in the literature, including patent literature.

The ensuing description will make reference chiefly to the side panels 3, it remaining for the rest understood that, except for what is explicitly indicated, what has been said as regards the panels 3 can apply also to the side panels 4 (if present).

As has already been said, the side panels 3 can possibly be made of an elasticated material, in particular with characteristics of "breathability", as described, for example, in the documents Nos. U.S. Pat. No. 6,572,595 or U.S. Pat. No. 6,994,761.

In various embodiments, the panels 3 can have a conformation that is as a whole tapered starting from their proximal edge 6 (which, as will be more clearly seen in what follows, is (indirectly) connected to the main body 2) towards the distal edge 7, which is shorter than the proximal edge 6, which in turn carries one or more closing formations 5, such as, for instance, closing systems initially folded to form a U that may extend towards the outside of the distal edge 7 of the side panel 3 so as to provide the connection with the side panels 4 situated at the opposite end of the central body 2 (or, in the case where the panels 4 are not envisaged, with the central body 2).

As has already been said, the connection formations 5 can be of an adhesive type or else formed so as to make a microhook or hook-and-loop (Velcro) connection with the panels 4 (or with the central body 2, in the absence of the panels 4) whether on account of the presence of complementary formations (not illustrated) on the panels 4 or on the surface of the body 2, or simply exploiting, for the purposes of the microhook connection, the loop formations constituted by fibres provided by the outer layer of the panels 4 or else of the body 2.

It will be noted that the individual panels 3 are to be applied in pairs of "twin" elements connected to the opposite sides of the main body 2 in a condition of specular symmetry with respect to the main longitudinal axis X1 of the article 1.

In various examples of embodiment considered herein, the panels 3 have a right-trapezial conformation, the proximal edges 6 and distal edges 7 of which form, respectively, the major base and the minor base. Various embodiments are suited to being used together with side panels that have conformations of a different type, as illustrated in the document No. EP-A-1 941 853 or in some of the documents cited in the corresponding research report.

Figure 2:
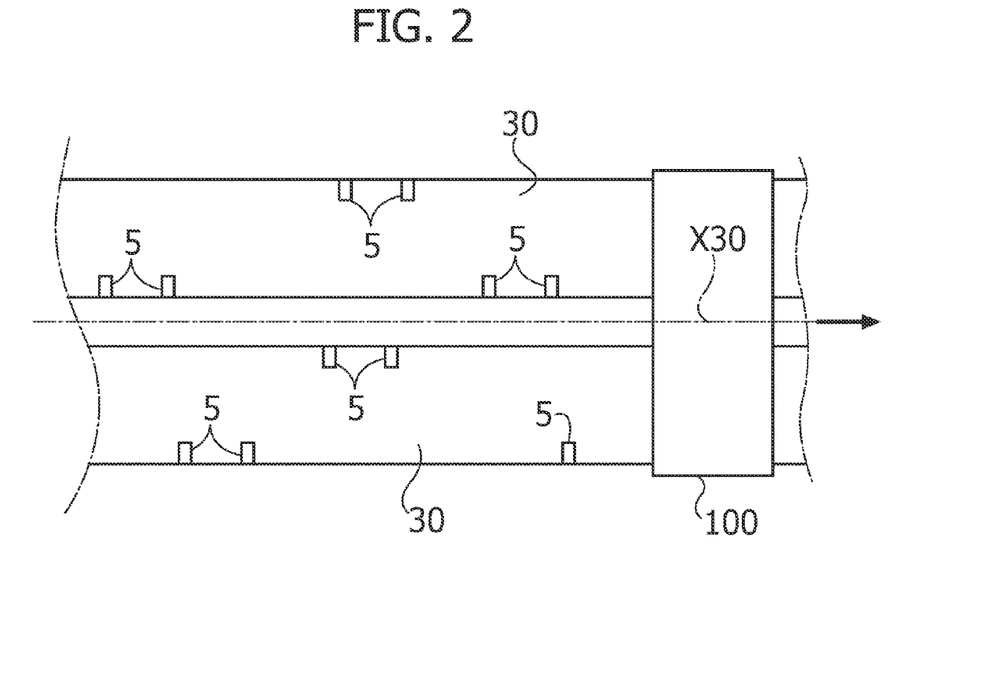
FIGS. 2 to 8 illustrate successive steps of a process according to one embodiment.

With reference initially to FIG. 2, the side panels 3 are formed (according to principles substantially similar to the ones described in the document No. EP-A-1 941 853—principles that will hence not be repeated herein in order to prevent rendering the present description unnecessarily laborious) starting from two web elements or strips 30 that advance in positions set alongside one another on opposite sides of a central axis X30. In various embodiments, the strips 30 can be made, for example, of an elasticated material with characteristics of breathability of the type already repeatedly mentioned previously and carry applied in alternating sequence on their opposite sides at distances corresponding to the average length of each side panel 3 (measured in the direction of the longitudinal axis X1 of the article 1, and hence in the direction of advance X30 of the webs 30) closing systems or "labels" 5, either single or multiple, of the type already described previously (adhesive, microhook means, etc.). The application of said formations 5 is made according to criteria in themselves known, which do not need to be described in detail herein: in particular, the formations 5 can be applied on opposite sides of each web 30, either in the context of an "on-line" operation that is to be followed—in the context of the same production process—by the subsequent operations described herein or in the context of an operation conducted "off-line", in conditions of time and/or space distinct from those of the subsequent operations described herein.

The webs 30, which, as viewed in FIG. 2, are assumed to be moving from left to right, are fed towards a cutting unit 100. Said cutting unit (which can be either a cutting unit of a mechanical type, for instance, with rotary blades, or a laser cutting unit, for example of the type described in the document No. EP-A-1 447 068 or else in the document No. EP-A-1 736 278) enables performing, in each web 30, in a position set between the formations 5, of cuts a and b—either rectilinear or shaped. In the example considered herein, which regards the production of side panels 3 shaped like a right trapezium, the cuts a extend in a direction generically oblique with respect to the direction of advance X30 of the webs 30, whilst the cuts b are orthogonal to the direction X30. It will on the other hand be appreciated that, just as the cuts a could also be orthogonal to the direction X30 (leading to the formation of rectangular side panels, such as, for example, the panels 4 visible in FIGS. 7 and 8), the cuts b could also be oblique with respect to the direction X30, leading to the formation of panels 3 shaped like an isosceles trapezium or a scalene trapezium.

Figure 3:
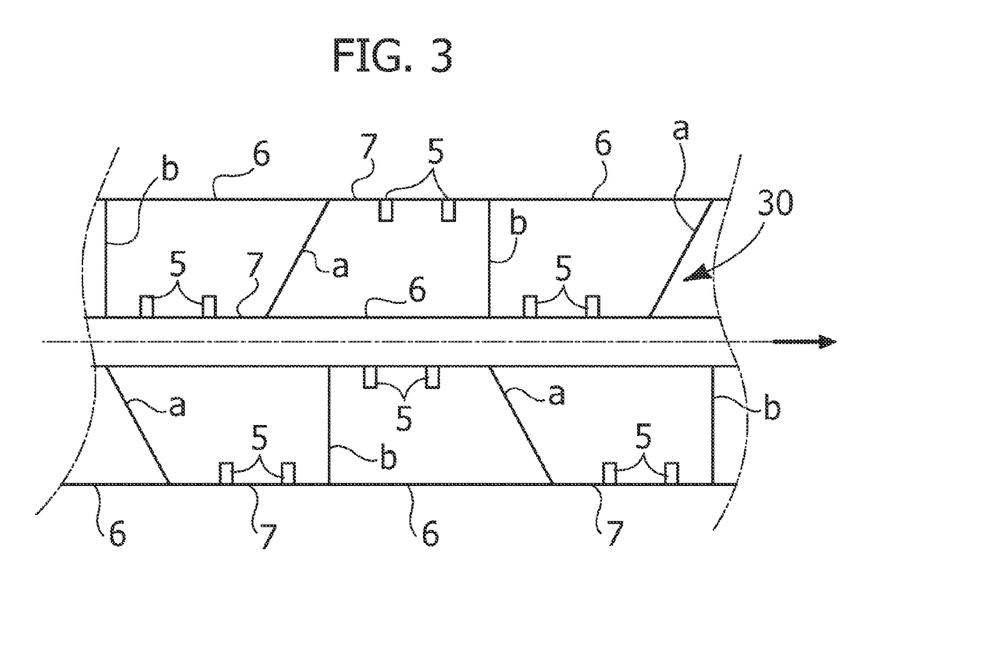

It will be appreciated that, unlike what is illustrated, for instance, in FIGS. 4 and 5 of EP-A-1 941 853, where the cuts a and b are made on the two webs 30 in a specularly symmetrical condition, in the embodiment represented herein in FIG. 3, even though the cuts a and b in the two webs 30 are as a whole aligned to one another (i.e., with a cut a in a web 30 more or less at the same height as that of a corresponding cut b in the other web 30) there is not obtained a cutting configuration that is exactly symmetrical.

In any case, at output from the cutting unit 100 in each of the webs 30 it is possible to recognize (as represented in FIG. 3) a chain of side panels 3 separated from one another by the cuts a and b, but in any case at the moment kept in a condition adjacent to one another, for example, on account of being withheld by suction means on a supporting drum or belt (not visible in the drawings).

In order to be applied on the central body 2 of a corresponding article 1, the panels 3 present in the two chains or webs 30 are hence subjected to an operation of repitching to bring them to a distance apart corresponding to the pitch of application on the articles 1, i.e., to the length of the articles 1 themselves.

In the case where at least one of the cuts a and b has been made oblique with respect to the direction of extension of the web 30 (axis X30), so that the panels 3 have a trapezial shape, in each web 30 there will be recognizable a chain or sequence of panels 3 that are the same as one another but set in alternating sequence: one rotated through 180° with respect to the preceding one (and with respect to the subsequent one) in the general plane of lie of the panels 3.

As may be seen in FIG. 3, in said sequence there will then be, alternated one after another:

a panel 3 with the smaller (distal) edge 7, which carries the formations 5, facing the other web/chain, and the larger (proximal) edge 6 opposite to the other web/chain; and a panel 3 with the larger (proximal) edge 6 facing the other web/chain and with the smaller (distal) edge 7, which carries the formations 5, opposite to the other web/chain.

In this case, in order to be applied on the central body 2 of a corresponding article 1, the panels that have the distal edge 7 that carries the formations 5 facing the other web/chain are subjected to an operation of rotation through 180° in the plane of lie.

Said movement of rotation through 180° imparted alternately on every other panel in each web or chain means that, after the movement of rotation, all the panels of each web or chain are all oriented in the same way prior to their application on the central body 2, to which the panels 3 are connected by their larger (proximal) edge, with the smaller (distal) edge 7 that carries the formations 5 facing the outside.

This orientation is initially available at output from the cutting unit 100 only for half of the panels (for instance, for the panel at the centre in the top part of FIG. 3 and for the two panels 3 at the sides in the bottom part of the same FIG. 3). For the other panels 3 (for instance, the two panels 3 in the outer position in the top part of FIG. 3 and the one in central position in the bottom part of the same FIG. 3) the aforesaid operation of rotation through 180° is carried out, for one panel 3 out of two (i.e., every other panel).

Figure 4:
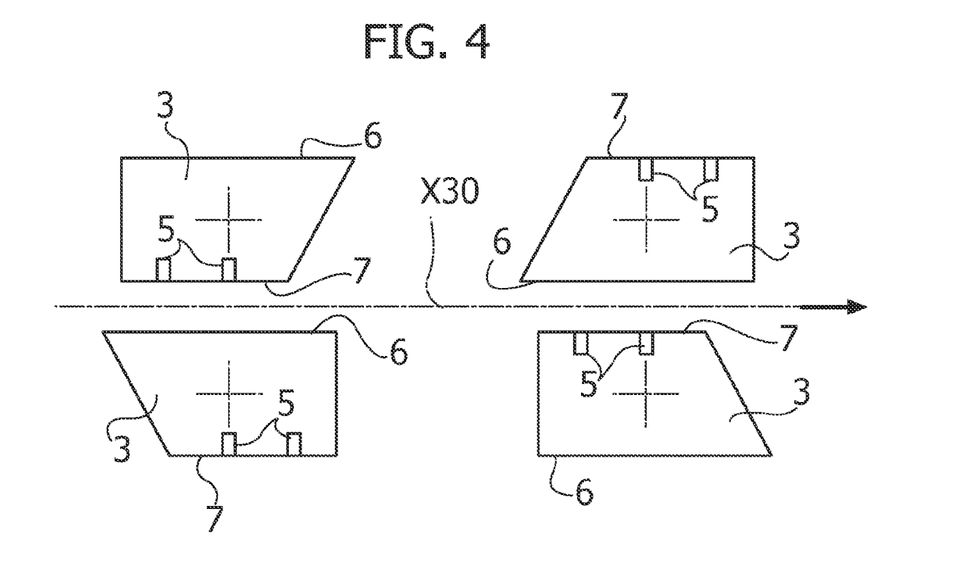
Figure 5:
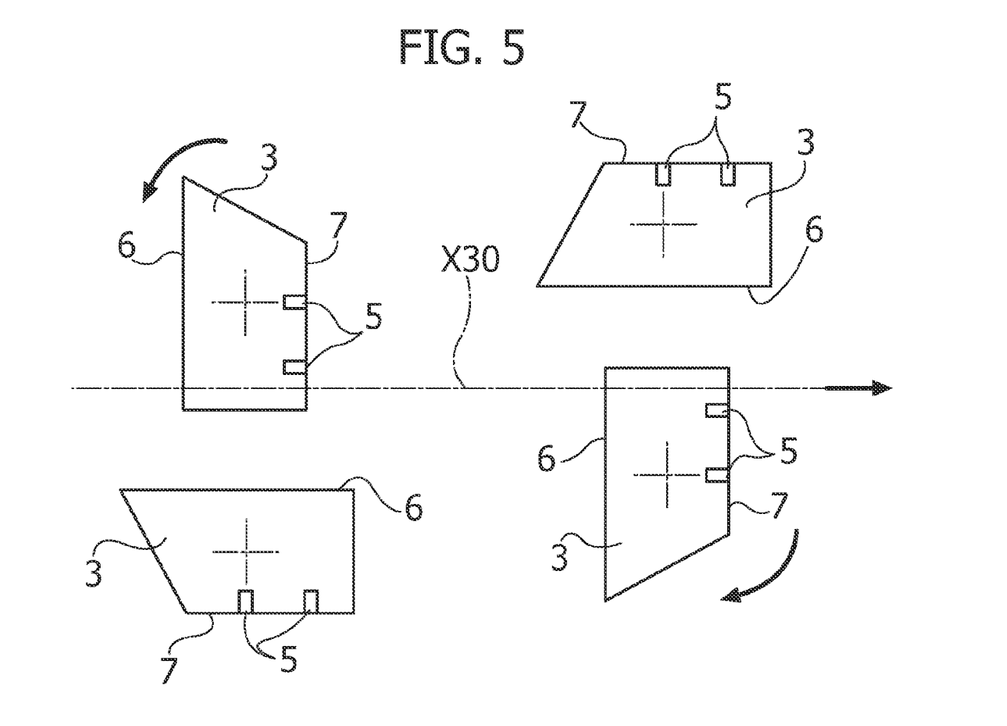

The embodiment referred to by way of example in FIGS. 4 and 5 envisages performing first the operation of repitching and then the operation of rotation.

This sequence of operations can be performed with means known in the art, for example, from EP-A-0 997 123, EP-A-1 179 495, EP-A-1 772 403. Another solution of rotator device for side panels is described in the document No. EP-A-1 719 484.

The operation of repitching can be conducted also in a number of successive steps, for example, with a first step that sets the panels 3 sufficiently apart to enable rotation of one panel out of two, preventing phenomena of mutual interference, with a subsequent repitching step in which the panels are brought to the final distance or pitch desired for the application on the central body 2.

Said final application pitch (achieved in one or more steps) can be rendered variable according to the characteristics of the article 1 considered so as to provide the so-called "change of format" function.

The operation of repitching carried out on the panels 3 of the two chains 30 can involve, as represented schematically in FIG. 4, also a operation of "phasing" of the panels 3 that are to be applied on opposite sides of the article 1, in such a way that, after the movement of rotation through 180° imparted on one panel out of two (see FIG. 5) the individual panels 3 are to be ordered in pairs of homologous side panels set aligned to one another (in phase) with specular symmetry as desired for their final application.

As may be appreciated from FIGS. 4 and 5, in various embodiments, the panels 3 not involved in the operation of rotation through 180° can be displaced laterally (for instance, moving away from the axis X30) so as not to hinder the movement of rotation of the "twin" panel.

Figure 6:
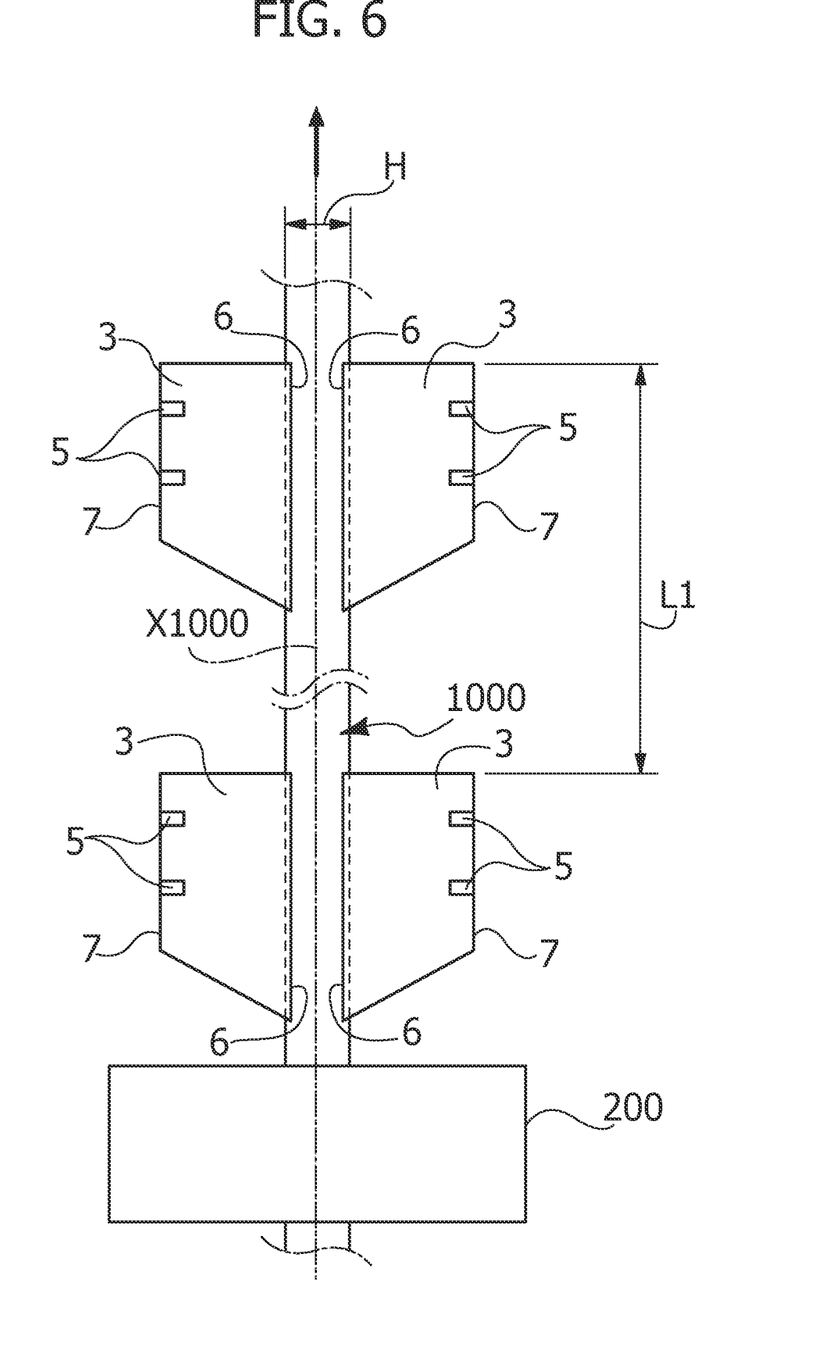

FIG. 6 illustrates the fact that the side panels 3 repitched and turned so as to be ordered in pairs of side panels that are specularly symmetrical with respect to the axis X30 are fed towards an application station 200 that applies them (for instance, through an operation of ultrasound sealing, heat-sealing, gluing, etc.) on an assembly web or "service" web 1000.

In various embodiments, the assembly web 1000 can have a width H smaller than the homologous dimension of width W of the central body 2. For instance, in various embodiments, the central body 2 can have a width W of approximately 70% of the width of one of the side panels 3, whilst in various embodiments the assembly web can have a width H equal approximately one half of the width of each side panel 3. In various embodiments, the assembly web 1000 has a width H of less than 32 cm, preferably of less than 8 cm.

In various embodiments, the assembly web 1000 is made of flexible laminar material, such as, for example, a nonwoven fabric of a type widely used in the sector of sanitary articles.

As on the other hand will be described more fully in what follows, it is also possible "to play" with the width H of the web 1000, for example, for carrying out operations of change of format.

The successive pairs of panels 3 are applied on the web 1000 at a distance L1 that takes into account the spaces necessary for performing the operations of cutting (segmentation) of the web 1000, which will be described more fully in what follows.

For instance, FIG. 6 refers ideally to a solution in which the successive pairs of panels 3 are applied on the web 1000 at a distance L1 corresponding basically to the length of the individual articles 1 that it is desired to produce.

As has already been said, said pitch value can be achieved, starting from the initial condition in which the panels 3 are adjacent to one another, in a single operation such as the one represented in FIG. 4 or else in a number of successive steps.

Figure 7:
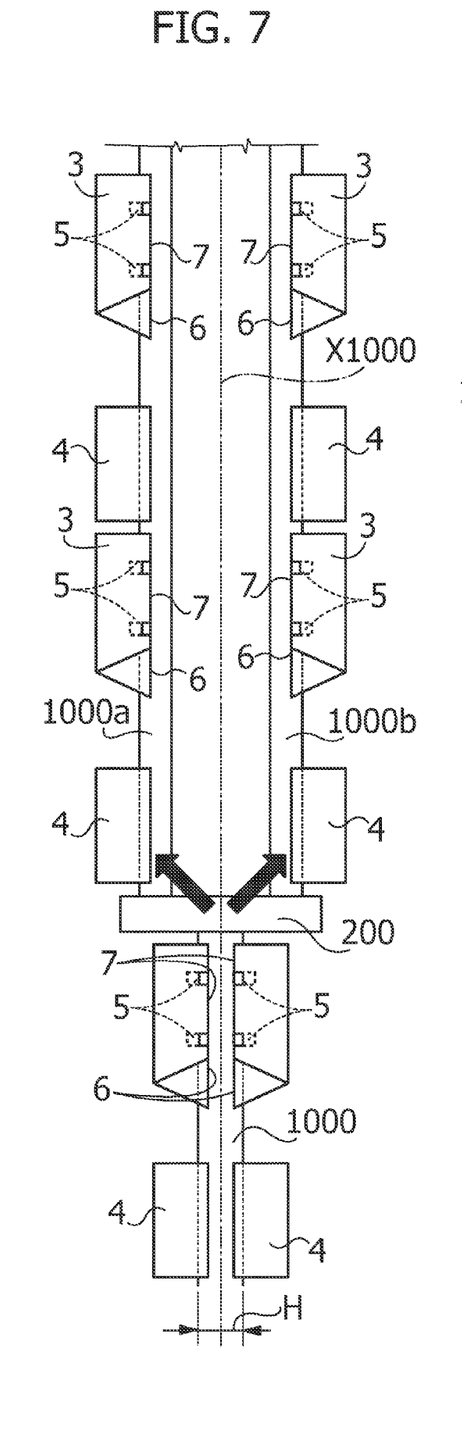

FIG. 7 is a schematic illustration of various operations of treatment to which the ensemble constituted by the assembly web 1000 on which the pairs of side panels 3 extending from opposite sides of the assembly web 1000 itself are applied can be subjected.

In particular, FIG. 7 shows that, by operating according to criteria in themselves known, the panels 3 can be folded on themselves according to a general V-shaped configuration by bringing their distal edge 7 approximately in the proximity of the proximal edge 6 (by "in the proximity" is meant that the aforesaid folding operation, which is designed to reduce the lateral encumbrance of the panels 3, does not necessarily imply an exact superposition of the edge 7 on the edge 6).

It will on the other hand be appreciated that the operations described previously with reference to the panels 3 can be performed also with reference to the panels 4 (if present): this applies, for example, to the operation of folding to form a V, which can be conducted in such a way that, after folding, the panels 3 and 4 all project by the same amount from the central body 2.

FIG. 7 highlights the possibility of applying rectangular side panels 4 on the assembly web 1000. These are hence panels that, with reference to the operation of segmentation represented in FIG. 3, have been obtained with cuts a, b extending in a direction orthogonal to the axis of advance X30. These are thus panels that, in themselves, may not require performance of the operation of rotation represented in FIG. 5: such an operation can on the other hand be anyway performed in the case where said panels have an elasticated structure with characteristics differentiated between their proximal edge and their distal edge (with reference to the condition of final installation on the central body 2) in order to obtain a symmetrical behaviour of the panels situated on the opposite sides of the article 1.

Possible advantages of various embodiments remain (for instance, in the case where articles 1—and hence the side panels 3, 4—of considerable dimensions are treated) also in the case where the operation of rotation represented in FIG. 5 is not envisaged.

The central part of FIG. 7 shows that the assembly web 1000, which carries applied thereon, set in pairs of specularly symmetrical elements, the panels (and the panels 4), is divided, in a station 200 (constituted, for example, by a fixed blade that acts on the assembly web 1000 in a position corresponding to its longitudinal median axis X1000), into two sub-webs 1000a, 1000b, each of which carries projecting from one side the side panels 3 and 4.

The two assembly sub-webs 1000a, 1000b can then be segmented and applied (once again by operating with different techniques such as gluing, ultrasound sealing, heat-sealing, etc., which are to be deemed in themselves known) on the two longitudinal sides of the chain of central bodies 2. Said operation is conducted (once again according to criteria in themselves known) in a station 300, which leads then to the assemblage of the structure of the article 1 represented in FIG. 1.

The chain of articles thus formed can then be segmented into individual articles 1 (by operating once again according to criteria in themselves amply known) with operations of transverse cutting made along lines A that extend in a transverse direction with respect to the direction of advance of the chain of articles, represented by the arrow X2. Each cutting line A is situated up against each pair of side panels 3 on the outer side of the individual article 1 thus obtained (i.e., with reference to the embodiments considered herein, in a position intermediate between a pair of side panels 3 and a pair of side panels 4 strictly adjacent thereto).

The description provided by way of example herein relates to modalities of production of the articles 1 of the "machine direction" (MD) type, in which the articles 1 are set with their longitudinal axis X1 oriented in the direction of advance of the articles 1 being formed. It will on the other hand be appreciated that the criteria underlying various embodiments are applicable also to modalities of production of the articles 1 of the "cross direction" (CD) type, where the articles 1 are set with their longitudinal axis X1 oriented transverse to the direction of advance of the articles 1 being formed.

Figure 8:
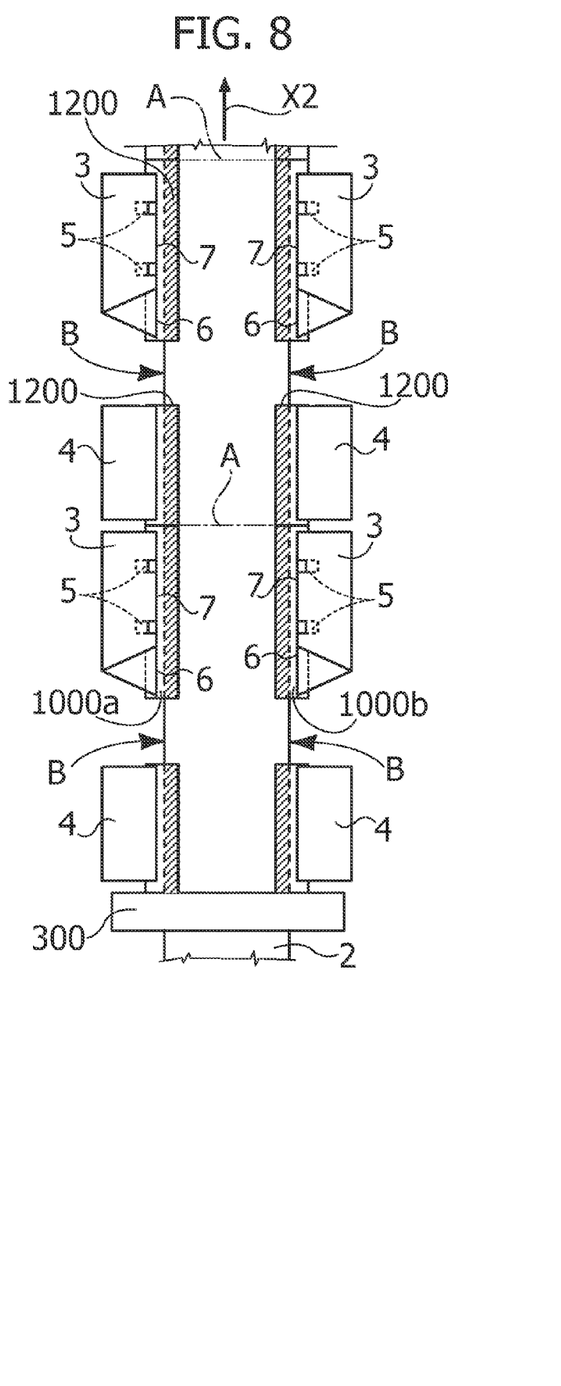

To ensure that the side panels 3 (and possibly 4) can maintain during the various operations represented in FIGS. 7 and 8 the folded V-shaped configuration possibly imparted thereon, it may be envisaged to form, between the edges 6 and 7 set on top of one another, a temporary connection constituted, for example, by a so-called "technical" or "green" glue, the action of retention of which can be easily overcome by the user at the moment in which he lays out the panels 3 in order to don the article 1, or, likewise, a connection obtained by means of heat-sealing or ultrasound sealing, which are both characterized by a pattern of sealing that enables an easy and complete opening of the panels, albeit guaranteeing closing thereof during the steps of production of the absorbent product.

In this regard, for reasons of clarity, it is recalled that:
the operation of folding of the panels 3 in a V (or possibly in another configuration, for example, a Z) to reduce the lateral encumbrance thereof is not at all imperative; and
the aforesaid folding operation for reducing the lateral encumbrance can possibly be performed also on the panels 4.

Figure 9:
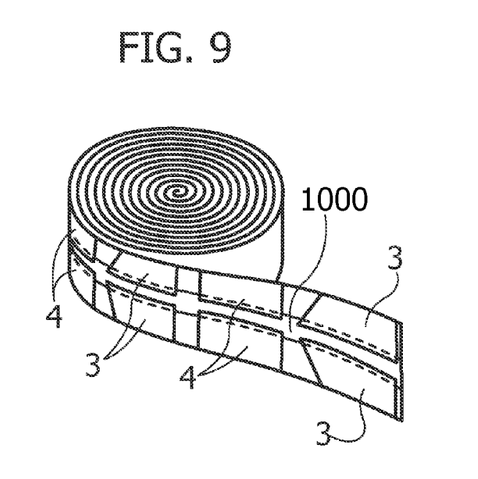
FIGS. 9 to 14 exemplify in a schematic way possible variant embodiments.

FIG. 9 and the subsequent figures highlight various aspects of the embodiments.

It will be appreciated that the aspects highlighted in said figures can in general be freely combined either together or with the various characteristics highlighted in FIGS. 1 to 8.

For instance, FIG. 9 highlights the fact that the assembly web 1000, which carries applied thereon the side panels 3 and the side panels 4 (if present), can constitute an "intermediate" product in itself, which is not necessarily to be sent on, immediately after its formation, to the subsequent operations of application on the central body 2. In particular, FIG. 9 is a schematic illustration of the fact that said product can, for example, be wound in a coil and be stored in view of subsequent use in a place and/or at a time different from the place and/or time in which it was formed.

Figure 10:
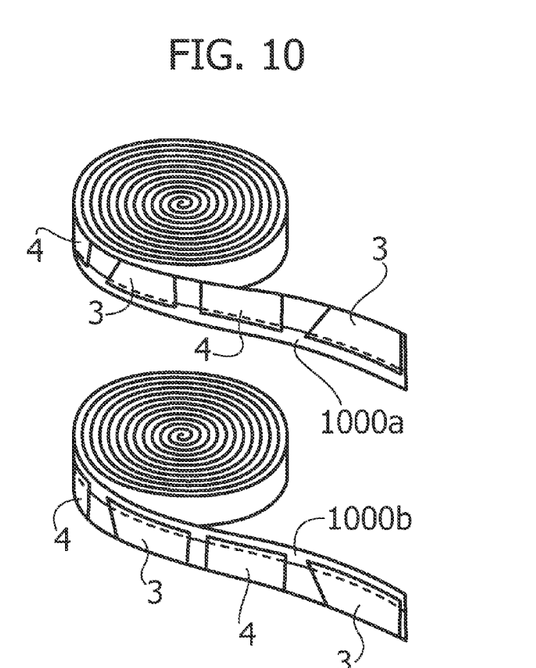

The operation of longitudinal cutting 200, instead of following, can precede the operation of application of the side panels 3 (and 4, if present), so that the half-webs 1000a and 1000b are formed before envisaging application of the panels 3 and (possibly) 4. FIG. 10 is a schematic illustration of the fact that, in this case, instead of envisaging a single assembly web 1000, which carries pairs of panels 3 (and 4, if present) projecting from the two sides of the assembly web 1000, there are provided instead two assembly (sub)webs 1000a and 1000b, each of which carries applied thereon, projecting from one side, the panels 3 (and 4, if present), respectively, "right" and "left", to be applied on the two sides of the central body 2.

Figure 11:
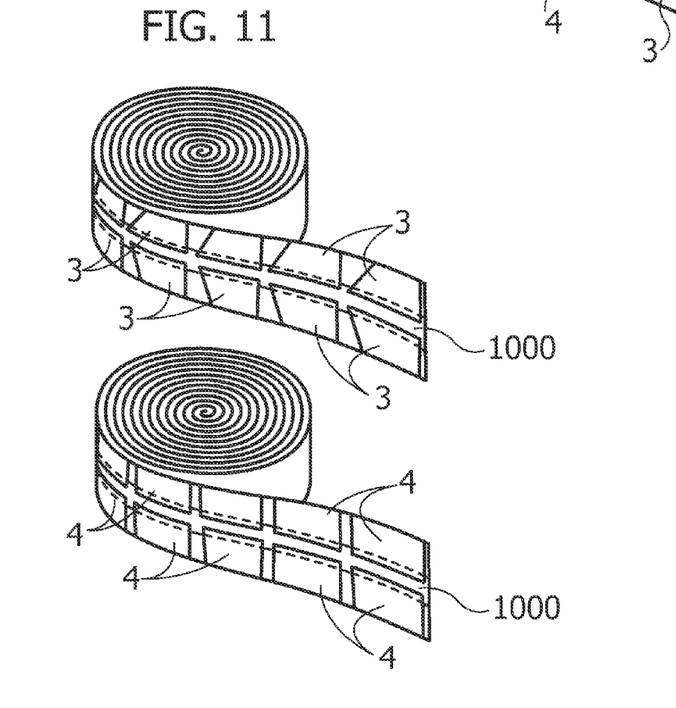

FIG. 11 is a schematic illustration of the fact that it is possible to provide:
- a first assembly web 1000, which carries the panels 3, for example, in pairs of panels projecting from its two sides; and
- a second assembly web 1000, which carries the panels 4, for instance, in pairs of panels projecting from its two sides.

In this case, the application of the side panels 3 and 4 is obtained (once again according to known criteria) in successive steps of intervention on the chain of the central bodies 2.

Figure 12:
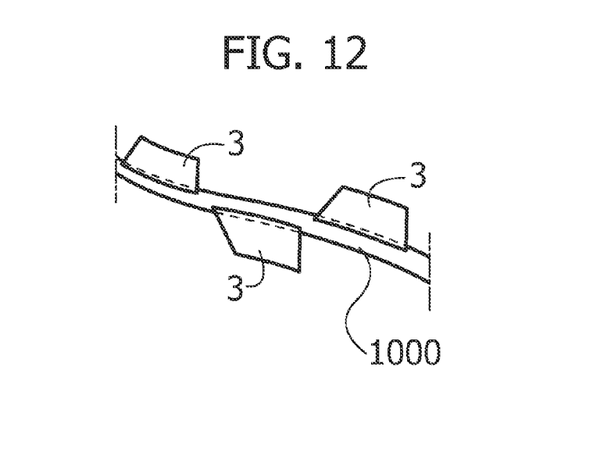

FIG. 12 shows that, in the case of panels 3 (and/or 4) projecting from the two sides of the assembly web 1000, in some embodiments it is possible to resort to a staggered application of panels 3 alternately projecting from one side and from the other. For instance, the "intermediate product" represented in FIG. 12 could be subjected to segmentation in successive lengths, each of which carries applied thereon a panel 3, with the flow of lengths sorted in two paths (one for each side of the central body 2, like what is illustrated in FIG. 7 for the two webs 1000a and 1000b). The lengths on the two sides of the central body 2 could then be subjected to repitching/rephasing in view of the subsequent application of pairs of symmetrical side panels 3 on the two sides of the central body 2.

Figure 13:
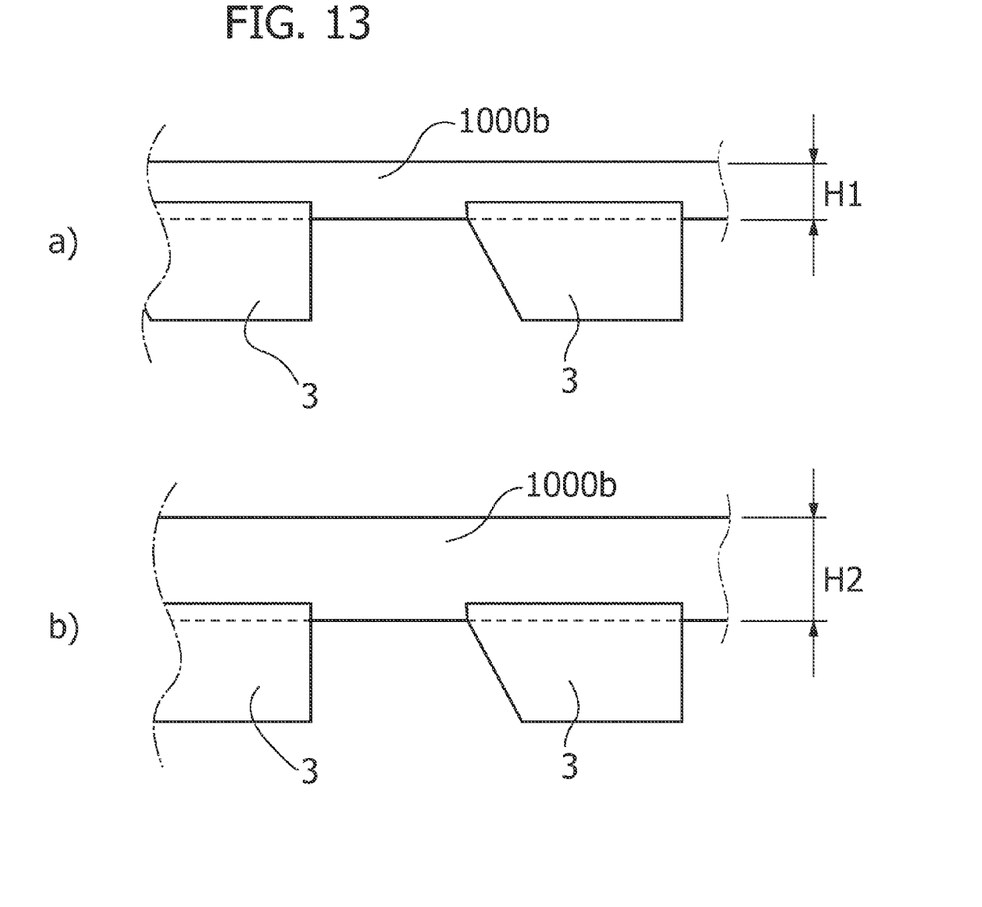

Again, FIG. 13 shows schematically that, independently of whether the side panels 3 (and possibly 4) are present on both sides or else even just on one side of the assembly web 1000, it is possible "to play" with the width H of said element (see, for example, H2>H1) to obtain a possible function of adaptation of the size of the article 1.

For instance, the part a) of FIG. 13 regards a solution in which the web 1000 (it may also be one of the webs 1000a and 1000b) is rather "narrow" H=H1. Once it has been applied (adhesively, by ultrasound sealing, heat-sealing, etc.) in 1200 on the central body 2 (see FIG. 1) with the respective side panels 3 (and 4, if present) connected thereto through the respective proximal edge, the assembly web 1000 practically "disappears", being only marginally visible within the overall structure of the article 1.

In this regard, FIG. 1 also shows the possibility of preventing a portion of web/half-web 1000a, 1000b from remaining in the area B comprised between the panels 3 and 4, i.e., in the area that are to define the bottom part of the openings for the user's legs: in said area, an elastication is in fact present (not explicitly represented in the drawings), which is designed to favour improved wearability of the article around the body of the user.

In the solution schematically represented in part b) of FIG. 13, the width H is chosen at a value H2>H1 in such a way that the webs 1000a and 1000b project laterally with respect to the central body by an extent selectively determined so as to contribute to producing a portion of the waistband 8 of the article 1.

Figure 14:
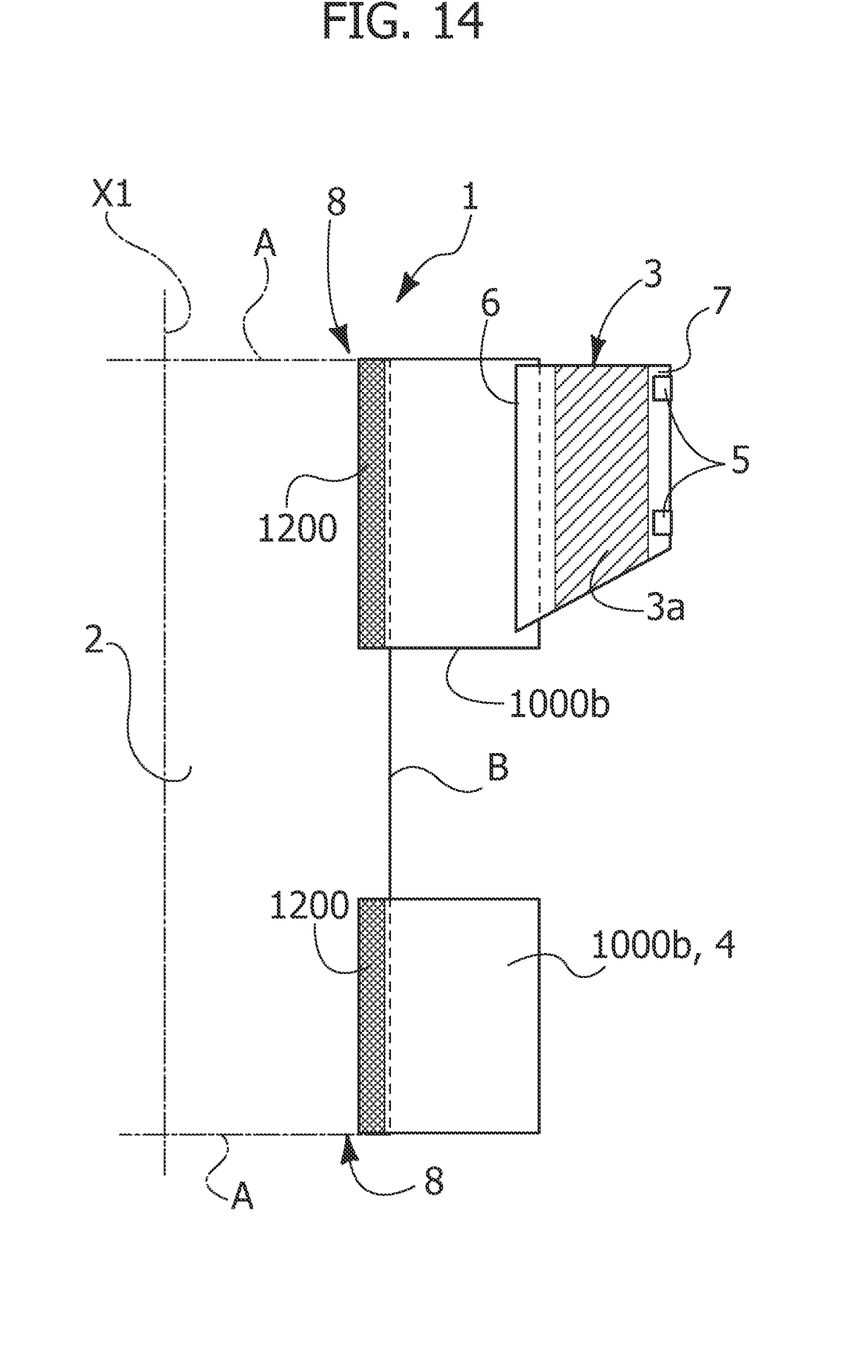

In FIG. 14, this possibility is highlighted at the level of article 1 as a whole, showing that, in some embodiments:
- in the side panels situated at one end (for example, the rear end) of the central body 2, the (half)web 1000b can have a width (measured in a direction orthogonal to the longitudinal axis X1) approximately equal to the homologous dimension of the panel 3 proper, which enables, for example, folding/overturning of the panel 3 (for example, the elasticated one in 3a) on the (half)web 1000b, facilitating folding of the article during packaging; and
- at the opposite end (for example, the front end) of the central body 2, the width (once again measured in a direction orthogonal to the longitudinal axis X1) of the (half)web 1000b is such as to cause the (half)web 1000b to be directly usable for making the panels 4.

Once again it is recalled that the individual aspects highlighted with reference to FIGS. 9 to 13, in addition to being freely combinable together, are also equally freely combinable with the various characteristics highlighted in FIGS. 1 to 8.

For instance, FIGS. 9 to 13 show that the pitch for application of the side panels 3 (and 4, if present) can be adjusted to a "provisional" value that is lower, even much lower, than the final desired pitch value L1 corresponding to the length of the articles 1 (see FIG. 6). The passage to the value L1 can be achieved with an operation of repitching performed immediately before application on the central bodies 2 performed, for example, by means of a unit of the type described in the document No. EP-A-1 864 768.

The adoption of this solution can present a dual advantage:
- in the first place, it enables reduction of the overall dimensions of the intermediate products (the assembly web 1000 with the panels 3 and/or 4 applied thereon), represented in FIGS. 9 to 13, reducing the dimensions thereof for the purposes of storage;
- in the second place, the "provisional" value can be chosen at a value as low as possible in such a way that, when the web 1000 or webs 1000a, 1000b are segmented in order to separate the individual side panels 3 (and, possibly, 4) from one another, to each panel 3 there will remain attached a length of web practically as long as the proximal edge of the side panel itself; this choice facilitates the operation of repitching designated by B in FIG. 1.

Of course, without prejudice to the principle of the invention, the details of implementation and the embodiments may vary, even significantly, with respect to what is illustrated herein purely by way of non-limiting example, without thereby departing from the scope of the invention as defined by the annexed claims. In particular, whereas the description provided by way of example herein relates at least implicitly to the production of articles that are made available "open" and then closed around the body of the user once worn (as occurs usually for articles for incontinent adults), various embodiments are suited to the production of articles that are to be made available "pre-closed", according to the modality commonly referred to (with reference to the articles for small children) as "training pants".

The invention claimed is:

1. A method of producing sanitary articles wearable as pants, the articles including:
   a central body to be arranged around the crotch portion of the user, said central body extending in a longitudinal direction between two opposed ends, and
   at least one pair of side panels connected to one of the ends of said central body and extending from opposite sides of said central body to define at least a portion of the waist line of the article,
   the method including:
   providing at least one assembly tape and applying onto said assembly tape a plurality of pairs of said side panels wherein each pair includes side panels extending from opposite sides of said assembly tape, and wherein each side panel has a proximal edge applied onto said assembly tape,
   connecting said side panels to said central body by connecting to said central body a portion of said assembly tape having at least one respective side panel applied thereon, whereby the proximal edges of said side panels are indirectly connected to said central body,
   longitudinally subdividing said assembly tape to form two further assembly tapes, each having a plurality of said side panels extending from one side thereof,
   connecting at least one pair of said side panels to said central body by connecting to the opposite sides of said central body portions of said further assembly tapes each having at least one respective side panel applied thereon.

2. The method of claim 1, including:
   providing at least one pair of assembly tapes with a plurality of said side panels extending from at least one side of each said assembly tapes, each side panel having a proximal edge applied onto an assembly tape,
   connecting said side panels to said central body by connecting to the opposite sides of said central body portions of said assembly tapes each having at least one respective side panel applied thereon.

3. The method of claim 1, including applying onto said assembly tape extending from at least one side of said assembly tape, a first plurality of first side panels and a second plurality of second side panels, said first side panels being different from said second side panels; said first side panels and said second side panels extending from said at least one side of said assembly tape as an alternate sequence of first and second side panels.

4. The method of claim 1, wherein each pair includes mirror-symmetrical side panels extending on opposite sides of said assembly tape.

5. The method of claim 1, including:
   forming at least one plurality of side panels to apply onto said assembly tape extending from at least one side of said assembly tape by segmenting a respective web element by cutting operations (a, b) at least part (a) of which is effected in an oblique direction with respect to the longitudinal direction of said respective web element, and
   imparting on every other panel of the side panels thus formed, in an alternate sequence, before applying them onto said assembly tape, a 180° rotation movement, whereby, after said rotation movement, the panels in said at least one plurality all have the same orientation to be applied onto said assembly tape.

6. The method of claim 1, including imparting onto at least one plurality of side panels to apply onto said assembly tape a V-fold to bring the distal edge of the side panel in proximity of the proximal edge of the side panel.

7. The method of claim 1, wherein said assembly tape has a width (H) less than 32 cm.

8. The method of claim 1, wherein said assembly tape is of a flexible laminar material.

9. The method of claim 1, including applying said side panels onto said assembly tape and connecting said assembly tape to said central body with an operation selected out of glueing, ultrasound welding, thermal welding.

10. A product for realizing the method of claim 1, said product including said assembly tape having applied thereon and extending from at least one side thereof a plurality of said side panels each having a proximal edge applied onto said assembly tape.

11. The method of claim 1, wherein said assembly tape has a width (H) less than 8 cm.

12. The method of claim 1, wherein said assembly tape is of a flexible laminar material, and wherein the flexible laminar material is a non-woven material.

13. A method of producing sanitary articles wearable as pants, the articles including:
   a central body to be arranged around the crotch portion of the user, said central body extending in a longitudinal direction between two opposed ends, and
   at least one pair of side panels connected to one of the ends of said central body and extending from opposite sides of said central body to define at least a portion of the waist line of the article,
   the method including:
   providing at least one assembly tape and applying onto said assembly tape a plurality of pairs of said side panels wherein each pair includes side panels extending from opposite sides of said assembly tape, and wherein each side panel has a proximal edge applied onto said assembly tape,
   connecting said side panels to said central body by connecting to said central body a portion of said assembly tape having at least one respective side panel applied thereon, whereby the proximal edges of said side panels are indirectly connected to said central body,
   imparting onto at least one plurality of side panels to apply onto said assembly tape a V-fold to bring the distal edge of the side panel in proximity of the proximal edge of the side panel,
   longitudinally subdividing said assembly tape to form two further assembly tapes, each having a plurality of said side panels extending from one side thereof,
   connecting at least one pair of said side panels to said central body by connecting to the opposite sides of said central body portions of said further assembly tapes each having at least one respective side panel applied thereon.

14. The method of claim 13, including:
   providing at least one pair of assembly tapes with a plurality of said side panels extending from at least one side of each said assembly tapes, each side panel having a proximal edge applied onto an assembly tape,
   connecting said side panels to said central body by connecting to the opposite sides of said central body portions of said assembly tapes each having at least one respective side panel applied thereon.

15. The method of claim 13, including applying onto said assembly tape extending from at least one side of said assembly tape, a first plurality of first side panels and a second plurality of second side panels, said first side panels being different from said second side panels; said first side panels and said second side panels extending from said at least one side of said assembly tape as an alternate sequence of first and second side panels.

16. The method of claim 13, wherein each pair includes mirror-symmetrical side panels extending on opposite sides of said assembly tape.

17. The method of claim 13, including:
forming at least one plurality of side panels to apply onto said assembly tape extending from at least one side of said assembly tape by segmenting a respective web element by cutting operations (a, b) at least part (a) of which is effected in an oblique direction with respect to the longitudinal direction of said respective web element, and
imparting on every other panel of the side panels thus formed, in an alternate sequence, before applying them onto said assembly tape, a 180° rotation movement, whereby, after said rotation movement, the panels in said at least one plurality all have the same orientation to be applied onto said assembly tape.

18. The method of claim 13, wherein said assembly tape has a width (H) less than 32 cm.

19. The method of claim 13, wherein said assembly tape is of a flexible laminar material.

20. The method of claim 13, including applying said side panels onto said assembly tape and connecting said assembly tape to said central body with an operation selected out of glueing, ultrasound welding, thermal welding.

21. A product for realizing the method of claim 13, said product including said assembly tape having applied thereon and extending from at least one side thereof a plurality of said side panels each having a proximal edge applied onto said assembly tape.

22. The method of claim 13, wherein said assembly tape has a width (H) less than 8 cm.

23. The method of claim 13, wherein said assembly tape is of a flexible laminar material, and wherein the flexible laminar material is a non-woven material.

24. A method of producing sanitary articles wearable as pants, the articles including:
a central body to be arranged around the crotch portion of the user, said central body extending in a longitudinal direction between two opposed ends, and
at least one pair of side panels connected to one of the ends of said central body and extending from opposite sides of said central body to define at least a portion of the waist line of the article,
the method including:
providing at least one assembly tape and applying onto said assembly tape a plurality of pairs of said side panels wherein each pair includes side panels extending from opposite sides of said assembly tape, and wherein each side panel has a proximal edge applied onto said assembly tape,
connecting said side panels to said central body by connecting to said central body a portion of said assembly tape having at least one respective side panel applied thereon, whereby the proximal edges of said side panels are indirectly connected to said central body,
providing at least one pair of assembly tapes with a plurality of said side panels extending from at least one side of each said assembly tapes, each side panel having a proximal edge applied onto an assembly tape,
connecting said side panels to said central body by connecting to the opposite sides of said central body portions of said assembly tapes each having at least one respective side panel applied thereon,
longitudinally subdividing said assembly tape to form two further assembly tapes, each having a plurality of said side panels extending from one side thereof,
connecting at least one pair of said side panels to said central body by connecting to the opposite sides of said central body portions of said further assembly tapes each having at least one respective side panel applied thereon.

* * * * *